United States Patent
Mishra

(10) Patent No.: US 7,608,258 B2
(45) Date of Patent: *Oct. 27, 2009

(54) METHOD FOR TREATMENT OF TENDINOSIS USING PLATELET RICH PLASMA

(76) Inventor: Allan Mishra, 1312 Orange Ave., Menlo Park, CA (US) 94025

( * ) Notice: Subject to any disclaimer, the term of this patent is extended or adjusted under 35 U.S.C. 154(b) by 232 days.

This patent is subject to a terminal disclaimer.

(21) Appl. No.: 11/085,987

(22) Filed: Mar. 22, 2005

(65) Prior Publication Data

US 2005/0186193 A1    Aug. 25, 2005

Related U.S. Application Data

(63) Continuation-in-part of application No. 10/941,124, filed on Sep. 15, 2004, now Pat. No. 7,314,617, which is a continuation of application No. 10/412,821, filed on Apr. 11, 2003, now Pat. No. 6,811,777.

(60) Provisional application No. 60/655,668, filed on Feb. 23, 2005, provisional application No. 60/372,682, filed on Apr. 13, 2002.

(51) Int. Cl.
*A01N 63/00* (2006.01)
(52) U.S. Cl. .................................. 424/93.72
(58) Field of Classification Search ............ None
See application file for complete search history.

(56) References Cited

U.S. PATENT DOCUMENTS

| | | | |
|---|---|---|---|
| 4,663,289 A | 5/1987 | Veech | |
| 4,931,395 A | 6/1990 | Griffin | |
| 5,079,236 A | 1/1992 | Drizen et al. | |
| 5,124,316 A | 6/1992 | Antoniades et al. | |
| 5,147,776 A | 9/1992 | Koerner, Jr. | |
| 5,165,938 A | 11/1992 | Knighton | |
| 5,178,883 A | 1/1993 | Knighton | |
| 5,269,290 A | 12/1993 | Barrett et al. | |
| 5,385,937 A | 1/1995 | Stamler et al. | |
| 5,403,272 A | 4/1995 | Deniega et al. | |
| 5,449,688 A | 9/1995 | Wahl et al. | |
| 5,474,891 A | 12/1995 | Murphy | |
| 5,494,590 A | 2/1996 | Smith et al. | |
| 5,510,102 A | 4/1996 | Cochrum | |
| 5,578,565 A | 11/1996 | Chao et al. | |
| 5,585,007 A | 12/1996 | Antanavich et al. | |
| 5,599,558 A | 2/1997 | Gordinier et al. | |
| 5,614,204 A | 3/1997 | Cochrum | |
| 5,643,786 A | 7/1997 | Cohen et al. | |
| 5,788,662 A | 8/1998 | Antanavich et al. | |
| 5,834,418 A | 11/1998 | Brazeau et al. | |
| 5,905,142 A | 5/1999 | Murray | |
| 5,935,850 A | 8/1999 | Clark et al. | |
| 6,063,297 A | 5/2000 | Antanavich et al. | |
| 6,098,631 A | 8/2000 | Holoshitz et al. | |
| 6,132,396 A | 10/2000 | Antanavich et al. | |
| 6,183,442 B1 | 2/2001 | Athanasiou et al. | |
| 6,214,338 B1 | 4/2001 | Antanavich et al. | |
| 6,242,594 B1 | 6/2001 | Kelly | |
| 6,280,473 B1 | 8/2001 | Lemperle et al. | |
| 6,306,171 B1* | 10/2001 | Conzemius | ............ 623/20.11 |
| 6,315,992 B1 | 11/2001 | Noh et al. | |
| 6,322,785 B1 | 11/2001 | Landeberg et al. | |
| 6,432,119 B1 | 8/2002 | Saadat | |
| 6,454,804 B1 | 9/2002 | Ferree | |
| 6,712,851 B1 | 3/2004 | Lemperle et al. | |
| 6,811,777 B2 | 11/2004 | Mishra | |
| 6,905,612 B2 | 6/2005 | Dorian et al. | |
| 2001/0031978 A1 | 10/2001 | Kipke et al. | |
| 2002/0006437 A1 | 1/2002 | Grooms et al. | |
| 2002/0032155 A1 | 3/2002 | Ferree | |
| 2002/0058030 A1 | 5/2002 | Monroy et al. | |
| 2002/0082220 A1 | 6/2002 | Hoemann et al. | |
| 2003/0116512 A1 | 6/2003 | Delbert et al. | |
| 2003/0152639 A1 | 8/2003 | Britton et al. | |
| 2003/0185812 A1 | 10/2003 | Ferree | |
| 2003/0192554 A1 | 10/2003 | Ferree | |
| 2003/0205538 A1 | 11/2003 | Dorian et al. | |
| 2003/0236573 A1 | 12/2003 | Evans et al. | |
| 2004/0126885 A1 | 7/2004 | Cines et al. | |

(Continued)

FOREIGN PATENT DOCUMENTS

EP    0 142 339    5/1985

(Continued)

OTHER PUBLICATIONS

Bales et al., "Microvascular supply of the lateral epicondyle and common extensor origin", J. Shoulder and Elbow Surgery 16 94) : 497-501 (2007).*

(Continued)

*Primary Examiner*—Sandra E Saucier
(74) *Attorney, Agent, or Firm*—Knobbe, Martens, Olson & Bear, LLP

(57) ABSTRACT

Methods and kits are disclosed to promote vascularization of tissue in mammals using an autologous platelet-rich plasma composition. The kit includes components for the preparation of platelet-rich plasma from the patient's blood and components for administration to an area in need of vascularization. The methods and kits are useful for the treatment of tendinosis, and in particular, lateral epicondylitis and plantar fasciitis.

12 Claims, 6 Drawing Sheets

U.S. PATENT DOCUMENTS

| | | | |
|---|---|---|---|
| 2004/0182795 | A1 | 9/2004 | Dorian et al. |
| 2004/0220101 | A1 | 11/2004 | Ferree |
| 2004/0220102 | A1 | 11/2004 | Ferree |
| 2004/0244806 | A1 | 12/2004 | Ferree |
| 2005/0043738 | A1 | 2/2005 | Ryan |
| 2005/0064042 | A1 | 3/2005 | Vunjak-Novakovic et al. |
| 2005/0186193 | A1 | 8/2005 | Mishra |
| 2006/0029578 | A1 | 2/2006 | Hoemann et al. |
| 2006/0041243 | A1 | 2/2006 | Nayak et al. |
| 2006/0127382 | A1 | 6/2006 | Mishra |
| 2006/0235306 | A1 | 10/2006 | Cotter et al. |
| 2006/0263407 | A1 | 11/2006 | Mishra |
| 2007/0014784 | A1 | 1/2007 | Nayak et al. |
| 2007/0037737 | A1 | 2/2007 | Hoemann et al. |
| 2007/0042016 | A1 | 2/2007 | Nayak et al. |
| 2007/0110737 | A1 | 5/2007 | Mishra |
| 2007/0122906 | A1 | 5/2007 | Mishra |

FOREIGN PATENT DOCUMENTS

| | | |
|---|---|---|
| EP | 0 417 818 | 3/1991 |
| JP | 61-502943 | 12/1986 |
| WO | WO 00/01427 | 1/2000 |
| WO | WO 02/15904 | 2/2002 |
| WO | WO 03/015800 | 2/2003 |
| WO | WO 2004/022078 | 3/2004 |
| WO | WO 2005/065242 | 7/2005 |

OTHER PUBLICATIONS

Chansky et al., "The vascularity of the rotator cuff", Clinics in Sports Medicine 10 (4) : 807-22 (1991).*

Durukan et al., "Acute ischemic stroke: Overview of major experimental rodent models, pathophysiology, and therapy of focal cerebral ischemia", Pharmacology, Biochemistry and Behavior 87 : 179-197 (2007).*

Playford et al., "Combined effect of coenzyme Q10 and fenofibrate on forearm microcirculatory function in type 2 diabetes", Atherosclerosis 168 : 169-179 (2003).*

Neisius et al., "Renal oncocytoma: Diagnostic and therapeutical consequences", Urologe Ausgabe A 32 (5) : 415-419 (1993).*

Hinkel, "The effect of irradiation upon the composition and vascularity of growing rat bones", A. J. Roentgenol. and Radium Therap. 50 (4) : 516-526 (1943).*

Pang et al., "Clinical implications of angiogenesis in cancers", Vascular Health and Risk Management 2 (2) : 97-108 (2006).*

Mooar et al., "The efficacy of autologous platelet gel administration in total knee arthroplasty: An analysis of range of motion, hemoglobin and narcotic requirement", poster # 148 presented at American Academy of Orthopaedic Surgeons 67th Annual Meeting, Orlando, FL, Mar. 15-19, 2000.*

Fylling et al., Multi-center clinical review: using autologous platelet gel for the treatment of diabetic plantar wounds:, Diabetes 50 (Supplement 2), A227 (Jun. 2001).*

Shvets, "Local injections of anesthetics and corticosteroids in the treatment of degenrative changes in the spine", Chirurgia narzadow ruchu i ortopedia polska 45 (3) : 259-63 (1980).*

Vassallo et al., "A Critical Comparison of Platelet Preparation Methods", Current Opinion in Hematology 13 : 323-330 (2006).*

Vasconcelos et al., "Quality of platelet concentrates derived by platelet rich plasma, buffy coat and apheresis", Transfusion and Apheresis Science 29 (1) : 13-16 (2003).*

Racz et al., "Buffy coat or platelet-rich plasma?", Vox Sanguinis 47 (2) : 108-13 (1984).*

Davies, Tennis Elbow, http://www.3-rx.com/tennis-elbow/treatment.php, May 4, 2001, accessed Dec. 11, 2008.*

Barrett, et al. "Growth Factors for Chronic Plantar Fasciitis?"*Podiatry Today*, pp. 37-42. Nov. 2004.

Edwards, et al. "Autologous Blood Injections for Refractory Lateral Epicondylitis," *The Journal of Hand Surgery*, pp. 272-278, vol. 28A, No. 2, Mar. 2003.

Eppley, et al. "Platelet Quantification and Growth Factor Analysis from Platelet-Rich Plasma: Implications for Wound Healing," *Plastic and Reconstructive Surgery*, pp. 1502-1508, vol. 114. No. 6, Nov. 2004.

Gruber, et al. "Platelets Stimulate Proliferation of Bone Cells: Involvement of Platelet-Derived Growth Factor, Microparticles and Membranes," *Clin. Oral Impl. Res*, vol. 13, pp. 529-535, 2002.

Marx, et al. "Platelet-rich Plasma—Growth Factor Enhancement for Bone Grafts." *Oral Surgery Oral Medicine Oral Pathology*, vol. 85, No. 6, pp. 638-646 Jun. 1998.

Price, et al. "Local Injection Treatment of Tennis Elbow—Hydrocortisone, Triamcinolone and Lignocaine Compared," *British Journal of Rheumatology*, vol. 30, pp. 39-44, 1991.

Cohen, et al. in *Principles of Surgery*, Chapter 8, "Wound Care and Wound Healing," pp. 263-295. (Seymore, et al. Editors), New York, 1999.

Snyder. et al. "Calcium-Dependent Proteolysis of Actin During Storage of Platelet Concentrates," *Blood*, vol. 73, No. 5, pp. 1380-1385, 1989.

Tang, et al. "The Effects of pCO2 and pH on Platelet Shape Change and Aggregation for Human and Rabbit Platelet-Rich Plasma," *Thrombosis Research*, vol. 10, No. 1, pp. 135-145, 1977.

Taylor, et al. "The Response of Rabbit Patellar Tendons After Autologous Blood Injection," *Medicine & Science In Sports & Exercise*, vol. 34, No. 1, pp. 70-73, 2001.

Floryan, et al. "Home Study Program: Intraoperative Use of Autologous Platelet-Rich and Platelet-Poor Plasma for Orthopedic Surgery Patients," *Aorn Journal*, vol. 80. No. 4. pp. 667-678, Oct. 2004.

Balk, et al. "Outcome of Surgery for Lateral Epicondylitis (Tennis Elbow): Effect of Worker's Compensation," *The American Journal of Orthopedics*, pp. 122-126, Mar. 2005.

Harvest Technologies GmbH Brochure for SmartPReP 2, 2002.

Website download from Medtronic, "Magellan" System Features and Benefits, 3 pages, 2004.

Cell Factor Technologies, Inc., Brochure for GPS II Platelet Concentrate System, 10 pages, 2004.

Cell Factor Technologies, Inc., Brochure for Boost Demineralizedbonematrix, 6 pages, 2004.

DePuy AcroMed, Inc. Brochure for Symphony Platelet Concentrate System, 10 pages, 2001.

Coiler, et al. "The pH Dependence of Quantitative Ristocetin-Induced Platelet Aggregation: Theoretical and Practical Implications—A New Device for Maintenance of Platelet-Rich Plasma pH," *Blood*, vol. 47, No. 5, pp. 841-854, May 1976.

Supplementary European Search Report dated Aug. 24, 2005.

Feuerstein, et al. "Congestive Heart Failure and Genomic Medicine: A Look into the 21st Century," *Cardiovascular Drugs and Therapy*, vol. 11, No. 6, 713-717, 1997.

Knebel, et al. "Heart Failure: State of the Art Treatment and Options," *Clinical Nephrology*, vol. 60, Suppl. 1, pp. S59-S66, 2003.

McCarthy, "New Surgical Options for the Failing Heart," *Journal of Heart Valve Disease*, vol. 8, No. 5, pp. 472-475, 1999.

Shim, et al. "Stem Cell Cardiomyoplasty: State of the Art," *Annals of the Academy of Medicine*, Singapore, Vol. 33, No. 4, pp. 451-460, 2004.

Martinez-Gonzalez, et al. "Do Ambulatory-Use Platelet-Rich Plasma (PRP) Concentrates Present Risks," *Medicina Oral*, vol. 7, pp. 375-390, 2002.

Cotter, et al. "A Novel Method for Isolation of Neutrophils from Murine Blood Using Negative Immunomagnetic Separation," *The American Journal of Pathology*, vol. 159, pp. 473-481, 2001.

Yang, et al. "Dielectric Properties of Human Leukocyte Subpopulations Determined by Electrorotation as a Cell Separation Criterion," *Biophysical Journal*, vol. 76, pp. 3307-3314, Jun. 1999.

Kahn, et al. "Overuse Tendinosis, Not Tendinitis, Part 1: A New Paradigm for a Difficult Clinical Problem," *The Physician and Sportsmedicine*, vol. 28, No. 5, 8 pages (no page numbers), May, 2000 (downloaded at http://www.physsportsmed,corn/issues/2000/05_00/khan.htm).

Cook, et al. "Overuse Tendinosis, Not Tendinitis, Part 2: Applying the New Approach to Patellar Tendinopathy," *The Physician and*

*Sportsmedicine*, vol. 28, No. 6, 12 pages (no page numbers), Jun. 2000 (downloaded at http://www.physsportsmed.com/2000/06_00khan.htm).

Khan, et al. "Histopathology of Common Tendinopathies: Update and Implications for Clinical Management," *Clinical Sports Medicine*, vol. 27, No. 6, 21 pages (no page numbers) 1999 (downloaded from http://www.clinicalsportsmedicine.com/articles/common_tendinopathies.htm).

Shigenobu, "Effects of Platelet-Derived Growth Factor on Lacerated Tendons," *Medical Magazine of Hiroshima University*, vol. 48, No. 1, pp. 1-16, 2000.

Okuda, "PRP (Platelet Rich Plasma . . . ," *Dental Outlook*, vol. 98, No. 4, pp. 874-875, 2001 with English translation.

Pierce, et al. "Platelet-derived Growth Factor and transforming Growth Factor-β Enhance Tissue Repair Activities by Unique Mechanisms," *The Journal of Cell Biology*, vol. 109, pp. 429-440, 1989.

\* cited by examiner

METHOD FOR TREATMENT OF TENDINOSIS USING PLATELET RICH PLASMA

RELATED APPLICATIONS

This application claims priority under 35 U.S.C. § 119(e) to provisional application No. 60/655,668 filed Feb. 23, 2005 and is a continuation-in-part of U.S. Application No. 10/941,124, filed Sep. 15, 2004, now U.S. Pat. No. 7,314,617, which is a continuation of U.S. Application No. 10/412,82 1, filed Apr. 11, 2003, now U.S. Pat. No. 6,811,777, which claims priority under 35 U.S.C. § 119(e) to U.S. Provisional Application No. 60/372,682, filed Apr. 13, 2002. All of the above are incorporated by reference in their entirety.

BACKGROUND OF THE INVENTION

1. Field of the Invention

Embodiments of the invention are directed to methods and kits for the treatment of damaged tissue in a human or non-human animal using autologous platelet-rich plasma. In a preferred embodiment, methods and kits are described for the treatment of lateral epicondylitis, plantar fasciitis, and rotator cuff injury.

2. Description of the Related Art

There is a need for treatment protocols for connective tissue injuries which are refractory to standard treatments such as anti-inflammatory medication, bracing, rest and physical therapy. Injuries or other damage to flexible, relatively avascular connective tissues (hereafter "connective tissue" or "connective tissues") are known to take a very long time to heal (months or even years). In many cases, injuries to connective tissues may never heal properly, necessitating surgical intervention. Connective tissue injuries and disorders have a significant impact on society. The overall prevalence of these problems is approximately 140 per 1000 persons in the United States, according to a 1995 survey by the National Center for Health Statistics. The same survey estimated the direct costs to be $88.7 billion and the indirect costs estimated to be up to $111.9 billion for lost productivity.

One example of a connective tissue disorder is tendinosis. Unlike tendonitis, tendinosis is not primarily an inflammatory condition. Tendinosis is an accumulation over time of small-scale injuries that don't heal properly; it is a chronic injury of failed healing. Tendinosis can occur in any tendon, with some of the most common areas being the hand, wrist, forearm, elbow, shoulder, knee, and heel. Tendinosis can result from repetitive activities such as playing sports, using computers, playing musical instruments, or doing manual labor. Some occupations that have increased risk for chronic tendon injuries include assembly line workers, mail sorters, computer programmers, writers, court recorders, data entry processors, sign language interpreters, cashiers, professional athletes, and musicians.

One specific type of tendinosis is lateral epicondylitis. Lateral Tendinosis (tennis elbow) is a common disorder which is seen in about 5 per 1000 patients in general practice. Although the etiology is not fully understood, it is typically seen in patients over the age of 35 as a result of some repetitive activity. The pathology underlying the disorder is related to overuse injury and microtearing of the extensor carpi radialis brevis tendon at the elbow. The body attempts to repair these microtears but the healing process is incomplete in many cases. Pathologic specimens of patients undergoing surgery for chronic lateral epicondylitis reveal a disorganized angiofibroblastic dysplasia. This incomplete attempt at repair results in degenerative, immature and avascular tissue. Incompletely repaired tissue is weaker than normal tendon tissue and lacks the strength to function normally. This tissue also limits the patient by causing pain and negatively impacting the patient's quality of life.

Another common tendinosis is Plantar fasciitis. While "plantar" means the bottom of the foot, "fascia" is a type of connective tissue, and "itis" means "inflammation", it is now thought that plantar fasciitis is not an inflammatory disorder. Furthermore, the plantar fascia is really a tendonous aponeurosis, not a fascial layer (Barrett, et al. (November 2004) Podiatry Today, pages 37-42).

The plantar fascia encapsulates muscles in the sole of the foot. It supports the arch of the foot by acting as a bowstring to connect the ball of the foot to the heel. When walking and at the moment the heel of the trailing leg begins to lift off the ground, the plantar fascia endures tension that is approximately two times body weight. This moment of maximum tension is increased if there is lack of flexibility in the calf muscles. A percentage increase in body weight causes the same percentage increase in tension in the fascia. Due to the repetitive nature of walking, plantar fasciitis may be a repetitive stress disorder similar to tennis elbow. It is common in several sub-groups of people, including runners and other athletes, people who have jobs that require a fair amount of walking or standing (especially if it is done on a hard surface), and in some cases it is seen in people who have put on weight—either by dietary indiscretion or pregnancy. Unfortunately, plantar fasciitis usually takes many months to resolve. According to statistics from the Southern California Orthopedic Institute, it takes approximately 6 months for 75% of people to recover from this problem.

The classic sign of plantar fasciitis is heel pain with the first few steps in the morning. The pain is usually in the front and bottom of the heel, but it can be over any portion of the bottom of the foot where the fascia is located. The pain can be mild or debilitating. It can last a few months, become permanent, or come and go every few months or years for the rest of a patient's life with no obvious explanation. Every year, about 1% of the population seeks medical help for this condition.

Similar incomplete repair may be present in other types of connective tissue injuries or damage, such as patellar tendonitis (Jumper's Knee), Achilles tendonitis (common in runners), and rotator cuff tendonitis (commonly seen in "overhead" athletes such as baseball pitchers), chronic injuries of the ankle ligaments ("ankle sprains"), or ligament tears. What is needed are compositions and methods for solving the problems noted above.

The pathophysiology of the above-mentioned conditions have been studied. Presently, many different non-operative and operative treatments exist. The non-operative measures include rest, activity modification, oral anti-inflammatory medication and cortisone injections. Rest and activity modification may help patients with some of these conditions, but there remains a significant clinical population that are not reachable with these therapies. Despite widespread use, oral anti-inflammatory medications have not proven to be useful in controlled studies. Some studies further suggest that non-steroidal medication may actually have an adverse effect on the healing process for ligament injuries. Also, no acute inflammatory cells have been found in pathologic samples of cases of lateral epicondylitis or plantar fasciitis. Cortisone injections are frankly controversial in the treatment of tendinoses and are contraindicated in acute ligament injuries. Several studies note an improvement in patients treated with cortisone in short term follow up. Results beyond one year, however, reveal a high symptom recurrence rate and only an equivocal efficacy rate. These injections also carry the risk of tendon rupture, infection, skin depigmentation, subdermal atrophy and hyperglycemia in diabetic patients.

Physical therapy is commonly used, but expensive and it is not clear that such treatment is helpful (Smidt 2003). Furthermore, the average cost is high: $1200-1500. Other treatment options include iontophoresis and extra corporeal shock wave (ECSW) therapy. Iontophoresis gave results better than placebo at 2 days (Nirschl 2003). ECSW Therapy has shown variable efficacy. This therapy was shown to be ineffective in a recent trial of 272 patients (Haake 2002). Chung and Wiley (2004) showed similar results with no difference between the control and the treatment group. A study on Botox vs Surgery showed no difference in outcome at 12 months. Both were effective. However, the study did not include a control group (Keizer 2002).

Operative measures include debridement and repair of the associated pathologic tendons. However, open or arthroscopic surgery has many potential complications such as deep infection, damage to neurovascular structures, and scar formation. The surgery is also expensive and carries the additional risks associated with regional or general anesthesia. Clearly there is a need for new treatment options in this area.

Platelet-rich plasma (PRP) is obtained from whole blood or plasma by concentrating the platelets from the blood. While whole blood may contain about 95% red blood cells, about 5% platelets and less than 1% white blood cells, PRP may contain 95% platelets with 4% red blood cells and 1% white blood cells. PRP can be combined with activating agents such as thrombin or calcium which activate the platelets to release their contents such as cytokinins and other growth factors. PRP has been used in medicine, primarily in bone grafting and dental implant applications and as part of a composition to use as a surgical adhesive. For example, Landesberg et al (U.S. Pat. No. 6,322,785) disclose an autologous platelet gel that includes PRP for bone grafts and dental implants. The PRP is activated by collagen and is applied topically to promote wound healing.

Antanavich et al. (U.S. Pat. No. 5,585,007) disclose preparation of PRP and use as a tissue sealant. Cochrum (U.S. Pat. No. 5,614,214) discloses a biopolymer that optionally includes PRP and its use to temporarily block arteries and veins. Gordinier et al. (U.S. Pat. No. 5,599,558) disclose a platelet releasate product, which includes platelets buffered to approximately pH 6.5, for use in a topical application to wounds.

None of the prior art teach treatment of connective tissue with PRP to promote tissue repair. Furthermore, Applicant has discovered that PRP has even broader application in treating a wide range of tissue injury and/or damage.

SUMMARY OF THE INVENTION

One embodiment of the invention is directed to a kit for vascularizing tissue with a platelet-rich plasma that is autologous, where the kit includes an anticoagulant to reduce blood coagulation; a disposable separating tube, adapted for use in a centrifugation device, for isolating platelet fractions from the blood; a pH adjusting agent to raise the pH of the platelet-rich plasma to a pH of between 6.5 and 8.0 creating a buffered platelet-rich plasma; and a platelet delivery device for applying the buffered platelet-rich plasma to tissue with a compromised blood supply to vascularize the tissue.

In preferred embodiments, the disposable separating tube includes a buoy to isolate platelet fractions. Preferably, the kit also includes a composition including a local anesthetic for numbing an area of tendinosis before administration of the buffered platelet-rich plasma composition. More preferably, the composition for numbing the area of tendinosis includes bupivicaine and epinephrine. Yet more preferably, the kit also includes an anesthetic delivery device for applying the local anesthetic.

In preferred embodiments, the kit includes instructions for isolation of platelets from the drawn blood using the disposable separating tube. In preferred embodiments, the kit includes instructions for administering the platelet-rich plasma composition to the area of tendinosis. In preferred embodiments, the anticoagulant is citrate dextrose anticoagulant solution and the pH adjusting agent is sodium bicarbonate. In preferred embodiments, the kit also includes a physical therapy aid to provide resistance for prescribed physical therapy.

Embodiments of the invention are directed to a kit for the treatment of tendinosis with an autologous platelet-rich plasma composition which includes an anticoagulant for preventing coagulation of blood; a disposable separating tube, adapted for use in a centrifugation device, for isolating platelet fractions from the blood; a pH adjusting agent to adjust the pH of the platelet-rich plasma composition to a pH of between 6.5 and 8.0 creating a buffered platelet-rich plasma composition; and a platelet delivery device for applying the buffered platelet-rich plasma composition to an area of tendinosis.

In preferred embodiments, the disposable separating tube includes a buoy to isolate platelet fractions. In preferred embodiments, the kit also includes instructions for isolation of platelets from the drawn blood using the disposable separating tube. In preferred embodiments, the kit also includes instructions for administering the platelet-rich plasma composition to the area of tendinosis. In preferred embodiments, the anticoagulant is citrate dextrose anticoagulant solution and the pH adjusting agent is sodium bicarbonate. In preferred embodiments, the kit also includes a physical therapy aid to provide resistance for prescribed physical therapy.

In preferred embodiments, the kit also includes a composition including a local anesthetic for numbing the area of tendinosis before administration of the buffered platelet-rich plasma composition. In more preferred embodiments, the composition for numbing the area of tendinosis includes bupivicaine and epinephrine. Yet more preferably, the kit includes an anesthetic delivery device for applying the local anesthetic.

In a highly preferred embodiment of the invention, the kit further includes a syringe for drawing blood, an apheresis needle, a tourniquet, a centesis needle, a skin antiseptic, and bandaging material.

Embodiments of the invention are directed to a method of vascularizing tissue with a compromised blood supply in a mammal which includes the steps of drawing autologous blood from the mammal; adding an anticoagulant to the autologous blood; fractioning the autologous blood in a disposable separating tube using a centrifugation device to isolate a platelet-rich plasma composition; titrating the platelet-rich plasma composition to obtain a pH of about 6.5 to 8.0 creating a buffered platelet-rich plasma; and administering the buffered platelet-rich plasma to tissue with a compromised blood supply, whereby platelet growth factors are released from the buffered platelet-rich plasma to promote vascularization.

Embodiments of the invention are directed to a method of treating tendinosis in a mammal which includes the steps of drawing autologous blood from the mammal; adding an anticoagulant to the autologous blood; fractioning the autologous blood in a disposable separating tube using a centrifugation device to isolate a platelet-rich plasma composition; titrating the platelet-rich plasma composition to obtain a pH of about 6.5 to 8.0 creating a buffered platelet-rich plasma composition; introducing a local anesthetic agent into and around a tendinosis site; and administering the buffered platelet-rich plasma composition to the tendinosis site, whereby platelet growth factors are released from the buffered platelet-rich plasma to promote vascularization at the tendinosis site.

In preferred embodiments of the method no exogenous activator is added to the platelet-rich plasma composition prior to its introduction into and around the site of tendinosis. In preferred embodiments, the composition which includes a local anesthetic agent also includes epinephrine. In preferred embodiments, the mammal is selected from horses, cows, sheep, pigs, dogs or cats. More preferably, the mammal is a human.

In preferred embodiments, the tendinosis is tennis elbow. In alternate preferred embodiments, the tendinosis is plantar fasciitis or rotator cuff injury.

Embodiments of the invention are directed to a method of treating plantar fasciitis in a human which includes the steps of drawing autologous blood from the human, adding an anticoagulant to the autologous blood, fractioning the autologous blood in a disposable separating tube using a centrifugation device to isolate a platelet-rich plasma composition, titrating the platelet-rich plasma composition to obtain a pH of about 6.5 to 8.0, thereby creating a buffered platelet-rich plasma composition, introducing a local anesthetic agent into a plantar surface of a foot, administering the buffered platelet-rich plasma composition to the plantar surface of the foot, whereby platelet growth factors are released from the buffered platelet-rich plasma composition to promote vascularization of the plantar surface of the foot.

In preferred embodiments, the method also includes limiting motion of the plantar surface of the foot for a therapeutic period. In preferred embodiments, an area to be treated is identified using ultrasound. In preferred embodiments, the buffered platelet-rich plasma composition is administered to a medial and/or central band of the identified fascia.

In preferred embodiments, no exogenous activator is added to the platelet-rich plasma composition prior to its introduction into and around the site of plantar fasciitis.

Embodiments of the invention are directed to a method of treating lateral epicondylitis in a mammal which includes the steps of administering a local anesthetic with an anesthetic delivery device to an affected elbow area, titrating a platelet-rich plasma composition to obtain a pH of about 6.5 to 8.0, and administering the buffered platelet-rich plasma composition into an affected elbow of the individual at an extensor carpi radialis brevis tendon.

In preferred embodiments, no exogenous activator is added to the platelet-rich plasma composition prior to its introduction into the affected elbow area.

In preferred embodiments, the method also includes performing physical therapy to promote vascularization of the affected tendon. In preferred embodiments, the method also includes revascularizing a site of compromised blood supply.

Embodiments of the invention are directed to a method of treating rotator cuff injury in a human. The method may include one of more of the steps: drawing autologous blood from the human; adding an anticoagulant to the autologous blood; fractioning the autologous blood in a disposable separating tube using a centrifugation device to isolate a platelet-rich plasma composition; titrating the platelet-rich plasma composition to obtain a pH of about 6.5 to 8.0 creating a buffered platelet-rich plasma composition; introducing a local anesthetic agent into a rotator cuff region of a shoulder; and administering the buffered platelet-rich plasma composition to rotator cuff tendons, whereby platelet growth factors are released from the buffered platelet-rich plasma composition to promote vascularization of the rotator cuff tendons. In preferred embodiments, the method also includes performing physical therapy to aid in promoting vascularization of rotator cuff tendons.

Embodiments of the invention are directed to a kit for the treatment of tendinosis with an autologous platelet-rich plasma composition where the kit includes a syringe for drawing blood; an apheresis needle; a tourniquet; a skin antiseptic; a citrate dextrose anticoagulant solution for preventing coagulation of the drawn blood; a disposable separating tube, adapted for use in a centrifugation device, for isolating platelet fractions from the blood; a buffering agent such as sodium bicarbonate, and the like to adjust the pH of the platelet-rich plasma composition to a pH of between 6.5 and 8.0 creating a buffered platelet-rich plasma composition; a composition for numbing the area of tendinosis such as bupivicaine and epinephrine, and the like; a platelet delivery device for applying the buffered platelet-rich plasma composition; bandaging material; instructions for isolation of platelets from the drawn blood using the disposable separating tube; and instructions for administering the platelet-rich plasma composition to the area of tendinosis. In preferred embodiments, the kit also includes a physical therapy aid to provide resistance for prescribed physical therapy.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

DETAILED DESCRIPTION OF THE PREFERRED EMBODIMENT

Figure 1:
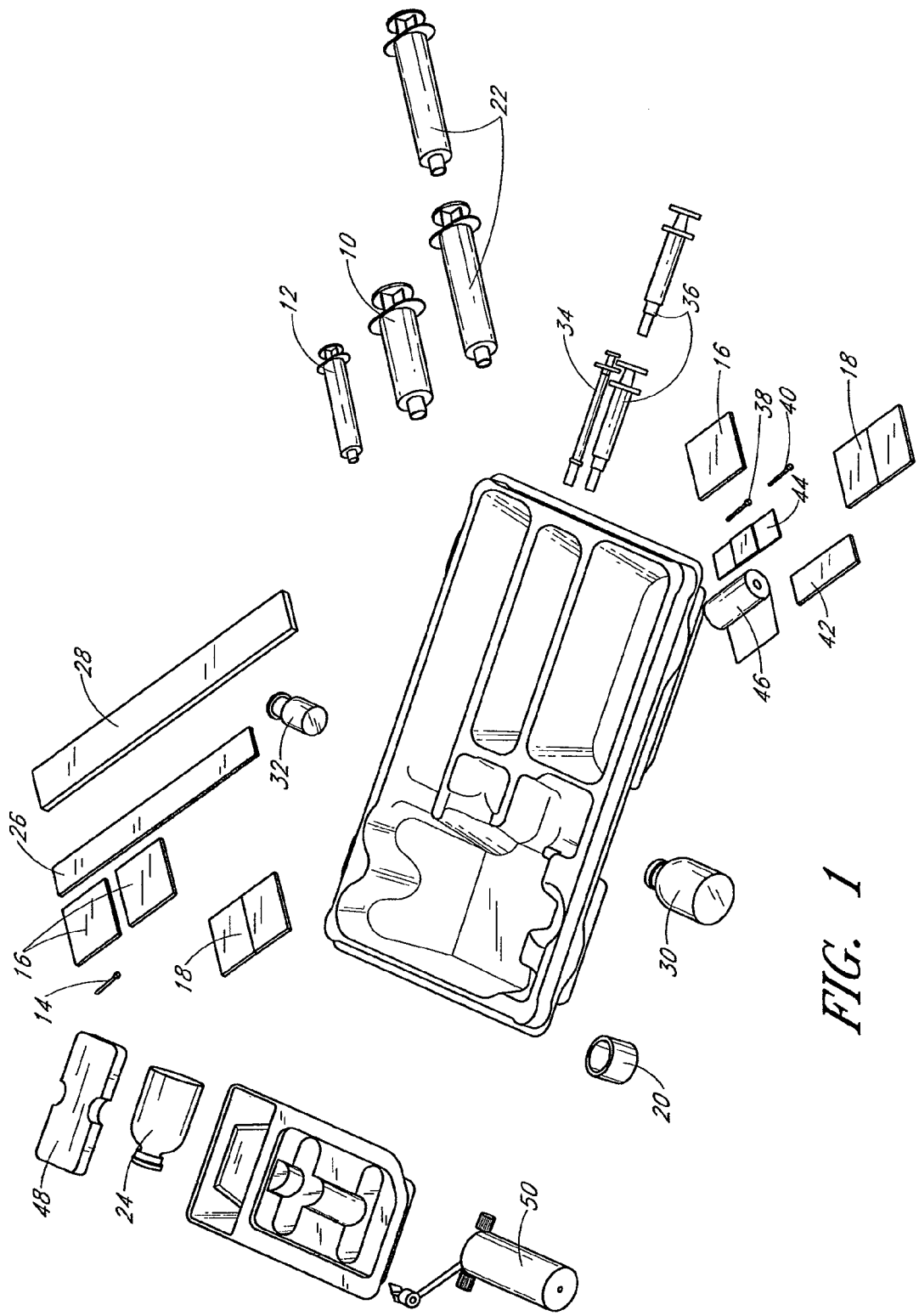
FIG. 1 shows an overhead view of a kit according to the invention.

Compositions and kits are needed for solving the problems noted above. Platelet-rich plasma (PRP) is an enriched platelet-containing mixture, isolated from whole blood, which is resuspended in a small volume of plasma, as defined in more detail below. Platelets are living but terminal cytoplasmic portions of marrow megakaryocytes. They have no nucleus for replication and will die off in 5-9 days. They adhere together to form a platelet plug at an injury site and actively extrude the growth factors involved in initiating wound healing. These growth factors, also called cytokines, are small proteins each of about 25,000 Daltons molecular weight. They are stored in a granules in platelets. In response to platelet to platelet aggregation or platelet to connective tissue contact, the cell membrane of the platelet is "activated" to release these alpha granules. These growth factors include platelet derived growth factors (PDGF), transforming growth factor beta 1 and 2 (TGF-β), fibronectin, vitronectin, fibrin and insulin-like growth factor (ILGF). These growth factors function to assist the body in repairing itself by stimulating stem cells to regenerate new tissue and by promoting vascularization.

The inventor has surprisingly discovered that certain inventive platelet compositions are useful for the treatment of several types of tissue damage or injury. As used herein, the term "injury" is a broad term and is used in the ordinary sense to refer, without limitation, to any tissue damage including a wound, trauma or lesion or any tissue degeneration. In particular, the inventive platelet compositions may be used to promote vascularization and/or revascularization of injured tissue and treatment of incomplete repair of various connective tissues, preferably tendinosis, most preferably lateral epicondylitis, plantar fasciitis, and rotator cuff injury.

The treatments and kits described herein are applicable to both human and non-human animals. The term "patient" as used herein refers to either a human or non-human patient. Particularly preferred applications are for veterinary animals such as horses, pigs, cows, sheep, cats and dogs. Most preferred embodiments are directed to treatment of human patients.

In one aspect, the invention relates to a method of treating incomplete repair in a patient's connective tissue comprising: obtaining a platelet composition; determining a lesion that comprises the incomplete repair in the patient's connective tissue; and minimally invasively introducing the platelet composition into and around the lesion. In an aspect, the invention relates to the method wherein the platelet composition is at or above physiological pH. In an aspect, the invention relates to the method wherein the platelet composition optionally includes platelet releasate. In an aspect, the invention relates to the method further comprising: mixing into the platelet composition one or more of the ingredients selected from thrombin, epinephrine, collagen, calcium salts, and pH adjusting agents. Also useful are materials to promote degranulation or preserve platelets, additional growth factors or growth factor inhibitors, small molecule pharmaceuticals such as NSAIDS, steroids, and anti-infective agents. In an aspect, the invention relates to the method wherein the patient's connective tissue is selected from: tendons, ligaments, joint capsules, and fascial tissues. More preferably, the tissue is a tendon. In an aspect, the invention relates to the method wherein obtaining the platelet composition comprises: drawing blood from a human or non-human animal; and centrifuging the blood to obtain a plasma-rich fraction. In an aspect, the invention relates to the method wherein the platelet composition comprises platelet-rich plasma. In an aspect, the invention relates to the method with the proviso that the platelet composition is substantially free from exogenous activators prior to its introduction into and around the region of the incomplete repair in the patient's connective tissue. In an aspect, the invention relates to the method wherein the platelet composition comprises platelets obtained from the patient.

The invention further relates to a method of treating incomplete repair in a patient's connective tissue comprising: obtaining a platelet composition; determining a lesion that comprises the incomplete repair in the patient's connective tissue; and introducing the platelet composition into and around the lesion, with the proviso that substantially no activator is added to the platelet composition prior to its introduction into and around the lesion. The invention also relates to the method wherein the platelet composition is minimally invasively introduced into and around the lesion. The invention also relates to the method wherein the platelet composition comprises platelet-rich plasma. The invention also relates to the method further comprising: mixing into the platelet composition substantially simultaneously with its minimally invasive introduction into and around the lesion one or more of the ingredients selected from thrombin, epinephrine, collagen, calcium salts, and pH adjusting agents. Also useful are materials to promote degranulation or preserve platelets, additional growth factors or growth factor inhibitors, small molecule pharmaceuticals such as NSAIDS, steroids, and anti-infective agents. The invention also relates to the method wherein the patient's connective tissue is selected from: tendons, ligaments, joint capsules, and fascial tissues. More preferably, the connective tissue is a tendon. The invention also relates to the method wherein introducing the platelet composition into and around the lesion comprises activating platelets in the platelet composition through the action of collagen present in the patient's connective tissue. The invention also relates to the method wherein the platelet composition is at or above physiological pH. The invention also relates to the method wherein the platelet composition comprises platelets obtained from the patient.

In yet another aspect, the invention relates to a composition comprising: platelet releasate wherein the composition is at a pH greater than or equal to physiological pH, and wherein the composition comprises substantially no unactivated platelets.

In a further aspect, the invention relates to a method of treating lesions resulting from acute injury to or chronic disorders of the Medial Collateral Ligament of the knee or elbow, Extensor Carpi Radialis Brevis tendon, Anterior Talofibular Ligament at the ankle, Achilles tendon, posterior tibial tendon, patellar tendon, quadriceps tendon, Anterior Cruciate Ligament, Posterior Cruciate Ligament, spinal ligaments, disc materials, rotator cuff tendons, or biceps tendons comprising: obtaining a platelet composition; determining a location of the lesion; and introducing the platelet composition into and around the lesion, with the proviso that substantially no activator is added to the platelet composition prior to its introduction into and around the lesion. In an aspect, the invention relates to the method wherein the platelet composition is minimally invasively introduced into and around the lesion. In an aspect, the invention relates to the method wherein the platelet composition comprises platelet-rich plasma. In an aspect, the invention relates to the method further comprising: mixing into the platelet composition substantially simultaneously with its minimally invasive introduction into and around the lesion one or more of the ingredients selected from thrombin, epinephrine, collagen, calcium salts, pH adjusting agents. Also useful are materials to promote degranulation or preserve platelets, additional growth factors or growth factor inhibitors, small molecule pharmaceuticals such as NSAIDS, steroids, and anti-infective agents. In an aspect, the invention relates to the method wherein obtaining the platelet composition comprises: drawing blood from a human or non-human animal; and centrifuging the blood to obtain a plasma-rich fraction. In an aspect, the invention relates to the method wherein the platelet composition is at or above physiological pH. In an aspect, the invention relates to the method wherein the platelet composition comprises platelets obtained from the patient.

In a further aspect, the invention relates to a method of treating lesions resulting from injury or chronic disorders of cardiac muscle, skeletal muscle, organ systems, vascular tissue, disc material, spinal bodies, spinal cord, and brain tissue comprising: obtaining a platelet composition; determining a lesion in need of treatment; and minimally invasively introducing the platelet composition into and around the lesion. In an aspect, the invention relates to the method wherein the platelet composition optionally includes platelet releasate. In an aspect, the invention relates to the method further comprising: mixing into the platelet composition one or more of the ingredients selected from thrombin, epinephrine, collagen, calcium salts, and pH adjusting agents. Also useful are materials to promote degranulation or preserve platelets, additional growth factors or growth factor inhibitors, small molecule pharmaceuticals such as NSAIDS, steroids, and anti-infective agents. In an aspect, the invention relates to the method wherein obtaining the platelet composition comprises: drawing blood from a human or non-human animal; and centrifuging the blood to obtain a platelet-rich fraction. In an aspect, the invention relates to the method wherein the platelet composition is at or above physiological pH. In an aspect, the invention relates to the method wherein the platelet composition comprises platelets obtained from the patient.

In an aspect, the invention relates to the method wherein the patient's connective tissue is selected from: tendons, ligaments, joint capsules, and fascial tissues. In an aspect, the invention relates to the method wherein obtaining the platelet composition comprises: drawing blood from a human or non-human animal; and centrifuging the blood to obtain a plasma-rich fraction. In an aspect, the invention relates to the method wherein the platelet composition comprises platelet-rich plasma. In an aspect, the invention relates to the method with the proviso that the platelet composition is substantially free from exogenous activators prior to its introduction into and around the region of the incomplete repair in the patient's damaged or injured tissue. In an aspect, the invention relates to the method wherein the platelet composition comprises platelets obtained from the patient.

The term "PRP" is used synonymously with platelet-rich plasma and as used herein, is a broad term which is used in its ordinary sense and is additionally defined for purposes of this application as a concentration of platelets greater than the peripheral blood concentration suspended in a solution of plasma Typically, platelet counts in PRP as defined herein range from 500,000 to 1,200,000 per cubic millimeter, or even more. PRP as defined herein comprises unactivated platelets. PRP is formed from the concentration of platelets from whole blood, and may be obtained using autologous, allogenic, or pooled sources of platelets and/or plasma. PRP may be formed from a variety of animal sources, including human sources. In preferred embodiments, PRP according to the invention is buffered to physiological pH.

Platelets are cytoplasmic portions of marrow megakaryocytes. They have no nucleus for replication; the expected lifetime of a platelet is some five to nine days. Platelets are involved in the hemostatic process and release several initiators of the coagulation cascade. Platelets also release cytokines involved with initiating wound healing. The cytokines are stored in alpha granules in platelets. In response to platelet to platelet aggregation or platelet to connective tissue contact, as would be expected in injury or surgery, the cell membrane of the platelet is "activated" to secrete the contents of the alpha granules. The alpha granules release cytokines via active secretion through the platelet cell membrane as histones and carbohydrate side chains are added to the protein backbone to form the complete cytokine. Platelet disruption or fragmentation, therefore, does not result in release of the complete cytokine.

A wide variety of cytokines are released by activated platelets. Platelet derived growth factor (PDGF), transforming growth factor-beta (TGF-β), platelet-derived angiogenesis factor (PDAF) and platelet derived endothelial cell growth factor (PD-ECGF) and insulin-like growth factor (IGF) are among the cytokines released by degranulating platelets. These cytokines serve a number of different functions in the healing process, including helping to stimulate cell division and promote vascularization/revascularization at an injury site. They also work as powerful chemotactic factors for mesenchymal cells, monocytes and fibroblasts, among others. For the purposes of this patent, the term "releasate" refers to the internal contents of the platelet, including cytokines, which have the potential to affect another cells' function.

Historically, PRP has been used to form a fibrin tissue adhesive through activation of the PRP using thrombin and calcium, as disclosed in U.S. Pat. No. 5,165,938 to Knighton, and U.S. Pat. No. 5,599,558 to Gordinier et al., incorporated in their entirety by reference herein. Activation results in release of the various cytokines and also creates a clotting reaction within various constituents of the plasma fraction. The clotting reaction rapidly forms a platelet gel (PG) which can be applied to various wound surfaces for purposes of hemostasis, sealing, and adhesion.

For instance, PG has been employed to assist with hemostasis in spine surgery and in a rat liver laceration model. One recent investigation showed that use of PG resulted in a significant reduction in post-op narcotic use, a reduction in post-op hemoglobin drop and faster return of functional range of motion after total knee replacement. PG has also been used in wound sealing. One study employed autologous PG as a sealant for craniotomy procedures and noted success in 39 out of 40 patients. PG has further been noted to augment bone healing. One controlled randomized prospective trial of 88 patients revealed a 2 fold increase in radiographic bone maturation and a 50% improvement in histologic bone density when PG was used (Marx, et al., Oral Surg. Oral Med. Oral Path. 1998, vol. 85(6): 638-646). In cardiac and vascular surgery PG is being employed to reduce the incidence of post-op wound dehiscence and infection (Kjaergard, et al., Eur J Cardio-Thoracic Surg. 1996, vol 10: 727-733; Slater, et al., J Ortho Res. 1995, vol 13: 655-663; Sumner et al. J. Bone Joint Surg. (Am) 1995, vol 77:1135-1147; Sethi, et al. Presented at International Society for the Study of Lumbar Spine, June 2001).

However, in none of the above applications and published documents has it ever been disclosed that PRP could be used surgically outside of the context of PG for any purposes other than platelet transfusions to a patient. It is one unique feature of this invention that platelets do not need to be activated prior to their introduction into a patient during the practice of the present invention.

In another embodiment, the inventive platelet composition may comprise releasate from platelets, in addition to platelets themselves. The releasate comprises the various cytokines released by degranulating platelets upon activation. Many activators of platelets exist; these include calcium ions, thrombin, collagen, epinephrine, and adenosine diphosphate. Releasates according to the invention may be prepared according to conventional methods, including those methods described in U.S. Pat. No. 5,165,938 to Knighton, and U.S. Pat. No. 5,599,558 to Gordinier et al.

One disadvantage of conventional releasate strategies associated with the use of PRP as PG is the use of thrombin as a preferred activator. In particular, much thrombin used in PG is bovine thrombin, which can create problems due to contamination issues regarding Creutzfeldt-Jakob disease. Many bovine materials are suspect due to possible prion contamination, and so use of bovine thrombin is disfavored in surgery.

Human pooled thrombin is likewise disfavored due to the potential of contamination with various materials such as viruses, prions, bacteria and the like. Recombinant human thrombin might also be used, but is quite expensive.

It is a particular advantage of the present invention that exogenous or extra activators need not be administered to a patient. Collagen, a major component of connective tissues, is a strong activator of platelets. Thus, when the inventive platelet composition is introduced into and/or around connective tissue, platelets in the platelet composition may bind to the collagen and then be activated. This reduces or eliminates the need for administering an exogenous activator such as thrombin. The disadvantages of thrombin use have been noted above. Other strong activators, such as calcium ions, can cause severe pain, unintentional clotting, and other undesirable side effects. Thus, in an embodiment of the invention, no or substantially no exogenous activator is present or added as part of the inventive platelet composition, or is used in the preparation of the inventive platelet composition. Of course, exogenous activators may still be employed if a physician determines that they are medically necessary or desirable.

The platelet composition may be prepared using any conventional method of isolating platelets from whole blood or platelet-containing blood fractions. These include centrifugal methods, filtration, affinity columns, and the like. If the platelet composition comprises PRP, then conventional methods of obtaining PRP, such as those disclosed in U.S. Pat. Nos. 5,585,007 and 5,788,662 both to Antanavich et al., incorporated herein by reference in their entirety, may be utilized.

The platelet-rich plasma composition may be delivered to an individual in need thereof by conventional means which include injection using a syringe or catheter. The platelet-rich plasma composition may also be delivered via a dermal patch, a spray device or in combination with an ointment, bone graft or drug. It may further be used as a coating on suture, stents, screws, plates or some other implantable medical device. Finally, it may be used in conjunction with a bioresorbable drug or device.

The site of delivery of the platelet-rich plasma composition is at or near the site of tissue injury and/or damage. The site of tissue injury or damage is determined by well-established methods including imaging studies and patient feedback or a combination thereof. The preferred imaging study used is determined by the tissue type. Commonly used imaging methods include, but are not limited to MRI, X-ray, CT scan, Positron Emission tomography (PET), Single Photon Emission Computed Tomography (SPECT), Electrical Impedance Tomography (EIT), Electrical Source Imaging (ESI), Magnetic Source Imaging (MSI), laser optical imaging and ultrasound techniques. The patient may also assist in locating the site of tissue injury or damage by pointing out areas of particular pain and/or discomfort.

Adjusting the pH of platelet compositions has been used to prolong the storage time of unactivated platelets, as disclosed in U.S. Pat. No. 5,147,776 to Koerner, Jr. and U.S. Pat. No. 5,474,891 to Murphy, incorporated by reference herein. pH may be adjusted using a variety of pH adjusting agents, which are preferably physiologically tolerated buffers, but may also include other agents that modify pH including agents that modify lactic acid production by stored platelets. Especially useful are those pH adjusting agents that result in the pH of the platelet composition becoming greater than or equal to physiological pH. In an embodiment, the pH adjustment agent comprises sodium bicarbonate. Physiological pH, for the purposes of this invention, may be defined as being a pH ranging from about 6.5-8.0, more preferably from 7.3 to 7.5, yet more preferably from about 7.35 to about 7.45. pH adjusting agents useful in the practice of this invention include bicarbonate buffers (such as sodium bicarbonate), calcium gluconate, choline chloride, dextrose (d-glucose), ethylenebis(oxyethylenenitrilo)tetraacetic acid (EGTA), monobasic phosphate, 4-(2-hydroxyethyl)-1-piperazineethanesulfonic acid (HEPES), maleic acid, 4-morpholinepropanesulfonic acid (MOPS), 1,4-piperazinebis(ethanesulfonic acid) (PIPES), N-tris(hydroxymethyl)methyl-2-aminoethanesulfonic acid (TES), tris(hydroxymethyl)aminomethane (TRIS BASE), tris (hydroxymethyl)aminomethane hydrochloride (TRIS.HCl), and urea. In a preferable embodiment, the pH adjusting agent is a bicarbonate buffer, more preferably, sodium bicarbonate.

For the purposes of this patent, the term "tissues" includes but is not limited to cardiac and skeletal muscle, disc material, vertebral bodies, internal organs, brain and spinal cord tissue, vascular tissue such as arteries and veins and non-differentiated tissue.

For the purposes of this patent, connective tissues comprise tendons, ligaments, fascial tissues, and joint capsules. In a preferable embodiment, connective tissues comprise the Medial Collateral Ligament of the knee or elbow, Extensor Carpi Radialis Brevis tendon (tennis elbow), Anterior Talofibular Ligament at the ankle, Achilles tendon, Anterior Cruciate Ligament, Posterior Cruciate Ligament, posterior tibial tendon, patellar tendon, quadriceps tendon, rotator cuff tendon, plantar fascia and biceps tendons.

Incomplete repair, as it is used in the context of this patent application, may be defined to mean repair that is disorganized, substantially non-existent (such as in the case of an unhealed tear), or otherwise pathological. Disorganized repair is characterized by a disorganized angiofibroblastic dysplasia, with degenerative, immature and avascular tissue. Such tissue is weaker than normal connective tissue and lacks the strength to function normally. This tissue also limits the patient by causing pain and negatively impacting the patient's quality of life. Substantially non-existent repair might occur in a situation where a connective tissue is torn and does not heal properly subsequently to the tear. Otherwise pathological repair may be any other type of repair in which the tissue is not repaired to be substantially the same as the tissue was before tissue repair was necessary.

Preferred embodiments of the invention are directed to a kit for the treatment of a tissue injury. In preferred embodiments, the tissue injury is a tendonitis or tendinosis. Preferably, the tendinosis is lateral epicondylitis (tennis elbow), plantar fasciitis, or rotator cuff injury. The kit contains components to draw blood, a tube to fractionate the blood in a centrifuge and components to apply PRP obtained from the tube for the treatment of the tendinosis. A preferred embodiment of a kit according to the invention is shown in FIG. 1.

Preferably, the kit and kit components are provided in a sterile condition with an expiration date. In preferred embodiments, the kit is sterilized by exposure to a minimum dose of 25 kGy gamma radiation or by ethylene oxide gas.

The kit includes materials for preparation of platelet-rich plasma and for administration of the PRP to an individual in need of treatment. In preferred embodiments, the kit includes a pH adjusting agent, preferably a sodium bicarbonate solution [30]. Preferably, the pH is adjusted to about 7.4. As used herein, the term "autologous platelet extract (APEX)" is used to refer to PRP with pH adjusted to physiological pH. Optionally, the kit may also include an exercise protocol and physical therapy aids such as a resistance band, e.g., Thera-Band®, exercise ball, or the like for further treatment of the injury after administration of APEX (not shown). A syringe and tourniquet are provided to draw blood for preparation of the PRP [10, 26]. One skilled in the art would be able to determine the amount of blood to withdraw for the specific injury treatment. Generally, 20-150 cc of blood is drawn, more preferably, 27-110 cc. In a preferred embodiment, 27 cc-55 cc of blood is withdrawn to provide platelets which are resuspended in 1-6 cc of PRP. However, larger or smaller quantities of blood or plasma may be used as the starting material to provide proportionally larger or smaller quantities of PRP (see Table 1 below). The blood or plasma may also be pooled from more than one source. In preferred embodiments, the platelet-rich plasma (PRP) is isolated from the patients own blood. In alternate embodiments the source may be allogenic, or pooled sources of platelets and/or plasma.

In preferred embodiments, the kit also includes an anticoagulant such as citrate dextrose solution [24]. The amount of anticoagulant in the kit depends upon the amount of blood drawn which depends upon the type of injury treated by the kit. One skilled in the art would know how much citrate dextrose to add to prevent blood coagulation for a given sample size. Typically for a 55 cc blood sample, 5 cc of citrate dextrose solution is added for anticoagulation. See Table 1 below.

TABLE 1

Amount of anti-coagulant and platelet yields for typical blood volumes (for GPS ® II Concentrator).

| Blood draw | 27 cc | 55 cc | 110 cc |
|---|---|---|---|
| ACD-A (citrate dextrose anticoagulant) | 3 cc | 5 cc | 10 cc |
| Platelet concentrate volume | 3 cc | 6 cc | 12 cc |

In preferred embodiments, the pH of the PRP is adjusted to physiological pH and the kit includes a ph adjusting agent. Preferably, the pH adjusting agent is a biocompatible buffer such as HEPES, TRIS, monobasic phosphate, monobasic bicarbonate, or any of the buffers described above, capable of adjusting the PRP to physiological pH. In preferred embodiments the pH is adjusted to between 6.5 and 8.0. In a most preferred embodiment, the kit includes a vial containing sodium bicarbonate solution, 1 mEq/ml (84 mg/mL), for adjusting the pH of the PRP to about 7.4 [30]. In most preferred embodiments, the platelet-rich plasma (PRP) is isolated from the patients own blood and is buffered to about pH 7.4. This buffered PRP is sometimes referred to herein as autologous platelet extract (APEX).

The kit preferably includes a local anesthetic such as anbesol, benzocaine, lidocaine, procaine, bupivicaine, or any appropriate anesthetic known in the art. In preferred embodiments, the anesthetic is bupivacaine HCl [32]. In preferred embodiments, the concentration of the bupivacaine HCl is 0.1-1%, preferably about 0.5%. In some preferred embodiments, the anesthetic includes epinephrine. Epinephrine is included at a ratio of 1:100,000 to 1:300,000. Preferably, epinephrine is included at a concentration of about 1:200,000.

The kit preferably includes syringes of appropriate size to draw blood from the patient for preparation of autologous PRP, and administration of the anesthetic and APEX compositions. Syringes useful in a preferred embodiment of the invention adapted for treatment of tennis elbow are provided in Table 2 below [10, 12, 14, 22, 28, 34, 36, 38, 40].

Additionally, the kit may include a sterilizing solution for treatment of the skin prior to administration of APEX such as iodine (betadine). In preferred embodiments, 3 betadine swab sticks are included in the kit [42]. The kit also includes bandaging material to stop any bleeding caused by the withdrawal of blood or injection of APEX into the patient such as gauze pads and/or bandaid(s) [16, 44].

Preferably, the kit includes a procedure instruction sheet and an exercise sheet including stretching and/or strengthening exercises for the patient. In some embodiments to facilitate appropriate strengthening exercises, a physical therapy aid such as a resistance therapy band, e.g, Thera-Band® strengthening tubing is included in the kit. For treatment of tennis elbow, typically a medium strength resistance therapy band is included.

In preferred embodiments, the kit includes a disposable separation tube that is adapted to be placed in a centrifugation device for concentrating platelets [48, 50]. An example of such a separation tube is the GPS® II and GPS® Mini disposable separation tube from Cell Factor Technologies, Inc. a wholly owned subsidiary of Biomet, Inc.

Optionally, the kit may also include a centrifuge for concentrating the platelets. Isolation of platelets depends upon the density difference between platelets and red blood cells. The platelets and white blood cells are concentrated in the layer between the platelet depleted plasma (top layer) and red blood cells (bottom layer). In the GPS® II or GPS® Mini platelet concentrate system, a bottom buoy and a top buoy are used to trap the platelet-rich layer between the upper and lower phase. This platelet-rich layer may then be withdrawn using a syringe or pipette. Generally, at least 60%, more preferably, at least 80% of the available platelets within the blood sample will be captured. These platelets are resuspended in a volume that is 3-20%, more preferably 5-10% of the sample volume.

A preferred embodiment of the kit described above is provided in the following Table 2 with reference to FIG. 1, which shows a possible packaging for a preferred embodiment of the kit.

TABLE 2

| KIT COMPONENTS FOR TREATMENT OF TENDINOSIS | Reference no. from FIG. 1 |
|---|---|
| 30 cc syringe (GPS ® Mini) or 60 cc syringe (GPS ® II) | 10 |
| 30 cc syringe, sterile with luer tip | 22 |
| 10 cc syringe, sterile with luer tip | 12 |
| 5 cc syringe, sterile with luer tip | 36 |
| 1 cc insulin syringe with 28 g × ½" needle | 34 |
| 18 g infusion cannula with clamp | 14 |
| 25 g × 1½" thin wall needle | 38 |
| 22 g × 1½" ultra thin wall needle | 40 |
| 18 g centesis catheter, sterile | 28 |
| Gauze, 2" × 2" pads | 16 |
| Alcohol prep pads | 18 |
| Adhesive tape, 1" × 1½" yd. Transpore tape | 20 |
| Citrate dextrose anticoagulant solution, U.S.P., Solution A (ACD-A) | 24 |
| Tourniquet, flat 1" × 18" | 26 |
| 50 ml vial sodium bicarbonate injection, USP (8.4%) | 30 |
| Bupivacaine HCl and epinephrine injection (0.5% bupivacaine HCl and epinephrine 1:200,000 injection | 32 |
| Povidone-iodine swab stick (3 pack) | 42 |
| 1" × 3" sterile bandage | 44 |
| GPS ® Mini disposable separation tube (30 cc) or GPS ® II (60 cc) | 48, 50 |
| Instruction sheet for preparation of PRP | |
| Instruction sheet for administration of PRP | |

In preferred embodiments, the kit is employed in the following method. PRP is prepared from either an autologous or allogenic source, or pooled sources of platelets and/or plasma. Preferably, an autologous source is used and the blood is withdrawn from a part of the body which is not involved with the procedure, such as an uninvolved arm. Typically, about 55 cc of blood is withdrawn into a 60 cc syringe [10] that contains 5 cc of the anticoagulant citrate dextrose solution [24]. In preferred embodiments, 5 cc of anticoagulant is drawn into a 60 cc syringe [10], attached to an apheresis needle, and primed with anticoagulant [24]. Blood (27 cc-55cc) is drawn from the patient using standard aseptic practice.

In preferred embodiments, the blood is then centrifuged using the Cell Factor Technologies GPS System® (or other similar system) following the instructions of the manufacturer. Typically, the blood-filled syringe containing 55 cc blood and 5 cc citrate dextrose is slowly transferred to a disposable separation tube [48, 50] which is loaded into a port on the GPS centrifuge. The sample is capped and placed into the centrifuge. The centrifuge is counterbalanced with 60 cc sterile saline, placed into the opposite side of the centrifuge. Alternatively, if two samples are prepared, two GPS disposable tubes are filled with equal amounts of blood and ACD-A [24]. The samples are centrifuged to separate platelets from blood and plasma. Typically, samples are centrifuged at about 2000-5000 rpm for 5 min. to 30 min. In a preferred embodiment, centrifugation is performed at 3200 rpm for extracted from a side isolated platelets are suspended in 3-5 cc plasma by agitation. The PRP is then extracted from a side port using a 10 cc syringe [12]. When starting with 55 cc of blood, normally about 5 cc of platelet-rich plasma is obtained.

The PRP is then buffered using the buffering agent [30] from the kit, preferably, 8.4% sodium bicarbonate for each cc of PRP, 0.05 cc of 8.4% sodium bicarbonate is added. For example, if 5 cc PRP is obtained, 0.25 cc of sodium bicarbonate would be added to provide the desired Ph of approximately 7.4. Table 3 below provides the appropriate quantity of 8.4% sodium bicarbonate. The syringe is gently shaken to mix the PRP and bicarbonate to form APEX.

TABLE 3

| PRP (cc) | 8.4% SODIUM BICARBONATE BUFFER (cc) |
|---|---|
| 1 | 0.05 |
| 2 | 0.10 |
| 3 | 0.15 |
| 4 | 0.20 |
| 5 | 0.25 |
| 6 | 0.30 |

For treatment of tennis elbow, the patient is placed in the supine position for preparation of tendon injection. The skin is sterilely prepped with the iodine swabs [42] from the kit. A numbing injection using an anesthetic such as bupivacaine HCl [32], optionally with epinephrine, from the kit is administered. Typically, about 2-3 cc of 0.5% bupivacaine HCl and epinephrine is injected superficially in the skin and dermis over the common extensor tendon origin using the 25 g needle [38] from the kit. Preferably, a small portion is injected into the tendon. A short period of time is allowed for the numbing injection to take effect, typically 1-5 min., preferably about 2 min.

The PRP is administered to the treatment area. 1-5 cc, preferably 2-3 cc, of the buffered PRP is injected into the extensor carpi radialis brevis tendon and surrounding area, using the 22 g needle [40] from the kit. In some embodiments, a small amount of bupivacaine and/or epinephrine can be placed into the syringe containing PRP prior to injection. Preferably, a single skin poke is used with multiple penetrations into the tendon (peppering technique). In a preferred administration for treatment of tennis elbow, 2 penetrations are made into the lateral epicondyle and 5 penetrations into the tendon.

Following the injection, the individual receiving the injection is kept in the supine position with the elbow supported for an appropriate time interval, preferably about 10-30 min. for treatment of tennis elbow, more preferably about 15-30 min., most preferably about 15-20 min. Typically, the patient is then sent home with a pain control agent such as Vicodin for use overnight. Tylenol is an alternate preferred pain control agent. Cold therapy/icing may also be used. Non-steroidal anti-inflammatory medication is not recommended post-operatively.

Preferably, the patient then begins a home exercise program using the instruction sheet provided in some embodiments of the kit and exercise band provided in some embodiments of the kit. Exercises may also be found at http://www.emedx.com. For tennis elbow, typically the stretching exercises are initiated 12-48 hours after the injection, more preferably about 24 hours after the injection. The strengthening program is started preferably 1-3 weeks after the injection, preferably at about 2 weeks after the injection. One skilled in the art would understand how to advise an individual on an exercise program. The nature of the exercise program and the time interval between the injection and starting the program would depend upon the nature and severity of the injury being treated.

Modifications according to the particular injury being treated are within the skill in the art. For example, the above procedure is readily adaptable to the treatment of plantar fasciitis. In the case of plantar fasciitis, however, it is preferred to immobilize the treated foot with a cast or brace for a period of up to one week, preferably about 2 days after the treatment. The patient may then add activities as tolerated and appropriate stretching and/or strengthening exercises are initiated.

It will be apparent to those skilled in the art that various modifications and variations can be made to the present invention without departing from the spirit or scope of the invention. Thus, it is intended that the present invention cover the modifications and variations of the present invention provided that they come within the scope of the appended claims and their equivalents. While the described methods and kits are believed to be widely applicable to a variety of injury treatments, this belief is in no way to be construed as an endorsement of off-label use of the kits and/or methods described herein. The following examples are illustrative of the present invention, and are not intended to limit it.

EXAMPLES

Example 1

PRP was prepared using a centrifuge unit made by Harvest (Plymouth, Mass.). (Similar units are available as The Cell Factor Technologies GPS system, the Depuy Symphony machine and the Medtronic Magellan machine.) Approximately 55 cc of blood was drawn from the patient using a standard sterile syringe, combined with 5 cc of a citrate dextrose solution for anticoagulation, and then spun down to isolate the platelets according to the manufacturer's protocol. These platelets were then resuspended in approximately 3 cc of plasma. The resulting platelet-rich plasma solution (PRP) was quite acidic and was neutralized with using approximately 0.05 cc of an 8.4% sodium bicarbonate buffer per cc of PRP under sterile conditions to approximately physiologic pH of 7.4. The PRP was not activated through addition of exogenous activators. This PRP composition is referred to herein as autologous platelet extract (APEX).

Example 2

Fifty cc of whole blood is drawn from a patient, and then prepared according to the method of Knighton, U.S. Pat. No. 5,165,938, column 3. The PRP is activated according to Knighton using recombinant human thrombin. The degranulated platelets are spun down and the releasate containing supernatant is recovered. The releasate may be optionally pH adjusted to a pH of 7.4 using sodium bicarbonate buffer.

Example 3

Thirty ml of whole blood were drawn from a patient. A platelet composition was prepared according to Example 1 of U.S. Pat. No. 5,510,102 to Cochrunm, incorporated herein by reference in its entirety, except that no alginate is added to the platelet composition.

Example 4

A study of the effects of the PRP compositions described herein was done using patients presenting with lateral epicondylitis (tennis elbow) which had failed non-operative treatment (anti-inflammatory medication, bracing rest and physical therapy). The patients were evaluated to obtain a visual pain score, a Mayo Elbow Score, and grip strength. For the visual analog pain score, zero equals "no pain" and 100 equals "the worst pain possible." The Mayo elbow score is an overall function score with a higher score indicating better overall function. The values of the two scores were statistically evaluated using a paired sample T test with significance set at $p<0.05$.

Individuals were selected for the study by the following criteria. All study participants had symptoms greater than 3 months and had failed non-operative treatment such as a standardized physical therapy protocol, NSAIDs, bracing, and cortisone injection (s). All study participants scored fair or poor by Mayo Elbow Score (pain, ROM, strength, ADLs). All study participants had pain greater than or equal to 60/100 on Visual Analog Score and no other systemic or local issues such as CTS, Shoulder Impingement, RA, Radiculopathy. Out of 140 consecutive patients evaluated, twenty (15%) met the strict inclusion criteria.

After obtaining informed consent, the patients were formally enrolled in the study and randomly assigned to either the APEX treatment group or control. Group 1 included patients treated with PRP (N=15). Group 2 included patients treated with Bupivicaine (N=5).

Each patient was then given 5 mg of Valium p.o. 30 minutes prior to the inventive tendon procedure. Patients were then prepped and draped in a sterile manner. A local anesthetic of 0.5% bupivicaine with epinephrine was infiltrated into the skin, subcutaneous structures and extensor carpi radialis brevis tendon. Care was taken to keep the local anesthetic out of the elbow joint.

Two to three minutes after administration of the local anesthetic, approximately 3-5 cc of the APEX composition of Example 1 was introduced into the extensor carpi radialis brevis tendon at the elbow via a 22 gauge needle. The control group received a numbing shot (Bupivicaine). Multiple punctures into the tendon approximately 0.5-1 cm from its origin were made. Promptly after the minimally invasive introduction of either the APEX composition of Example 1 or the numbing shot, the patient's arm was immobilized at about 90% of flexion without elevation of the arm or hand. The surgical area was then sterilely dressed and the patient asked not to move their arm for 30 minutes. Each patients' neurovascular, pain and function status was evaluated shortly after the injection, and at 30 minutes following the end of the procedure. Patients in the study received no NSAIDs or other treatments. They were instructed to follow a standardized stretching and strengthening program at 2-3 days after the procedure and to return to activities as tolerated at 4 weeks. The visual pain score, Mayo Elbow Score, and grip strength were all monitored post-procedure.

Figure 2:
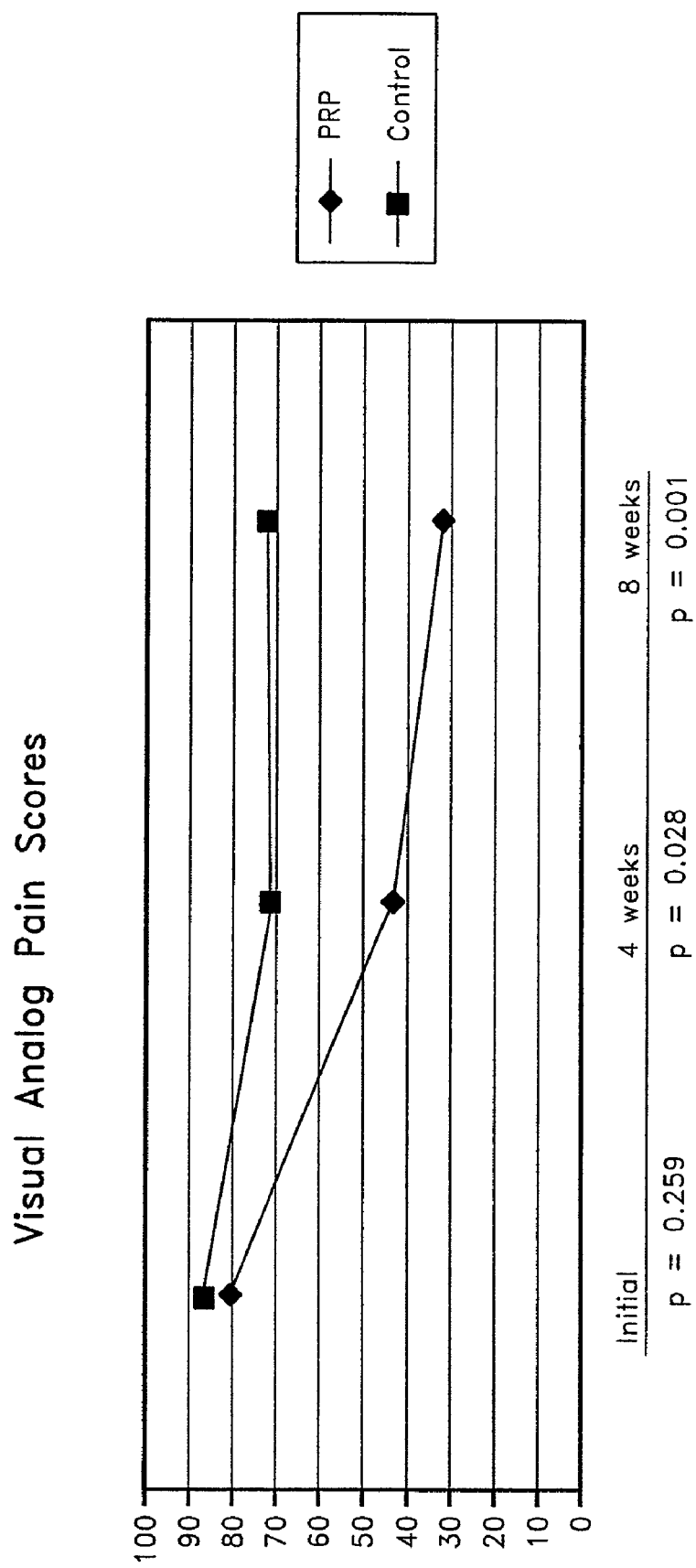
FIG. 2 shows the average visual pain scores before treatment and at 4 and 8 weeks post-treatment for tennis elbow. N=15 for the PRP-treated group; N=5 for control group.

The results are shown in FIG. 2 for the Visual Analog Pain scores at 4 and 8 weeks. FIG. 2 indicates a 46% improvement in the APEX treated group compared with 17% improvement for the control. At 8 weeks, there was a significant 60% improvement in the APEX treated group compared with only 16% improvement in the control group.

Figure 3:
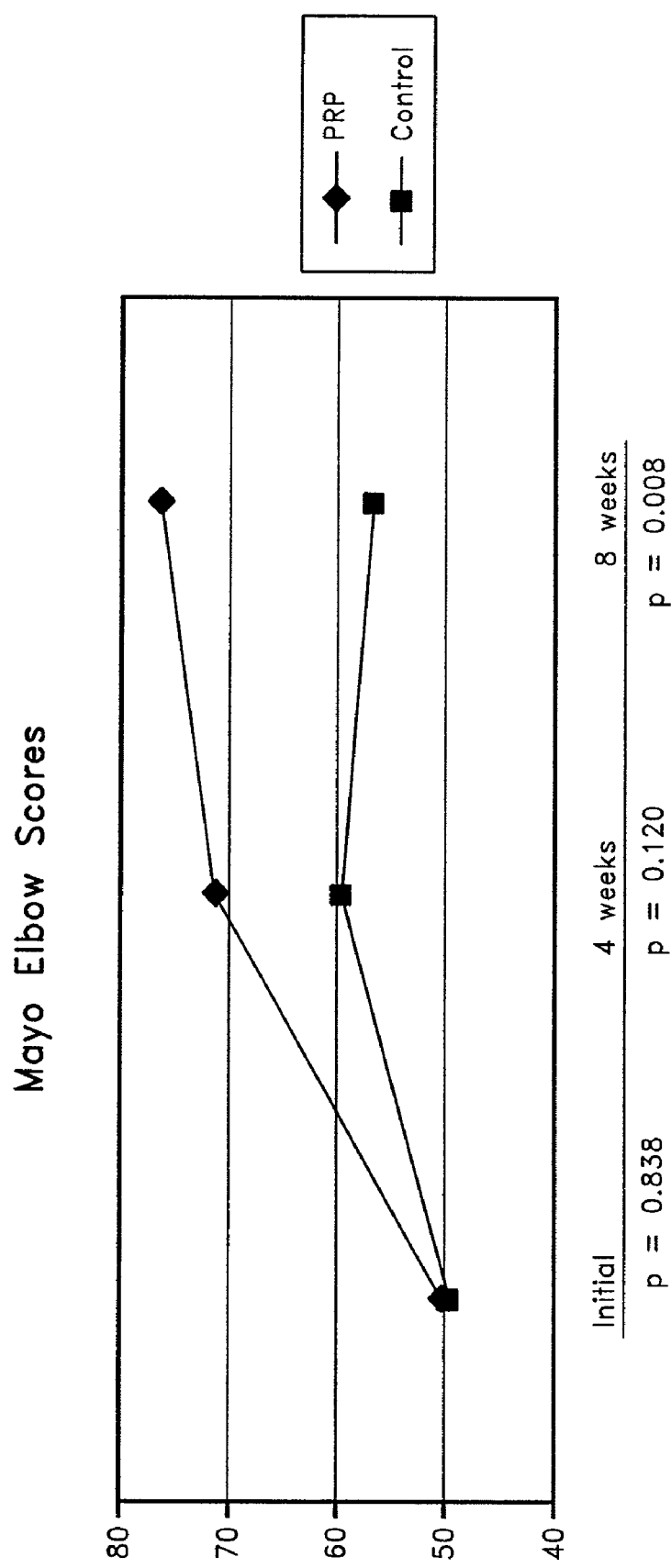
FIG. 3 shows the average Mayo elbow scores before treatment and at 4 and 8 weeks post-treatment. N=15 for the PRP-treated group; N=5 for control group for tennis elbow.

Mayo elbow scores are shown in FIG. 3. FIG. 3 indicates a 42% improvement in the APEX treated group compared to 20% improvement in the control at 4 weeks. At 8 weeks, there is an increased improvement of 52% in the APEX treatment group and only a 14% improvement in the control group. After 8 weeks, 60% of the control patients either sought treatment outside the protocol or formally withdrew from the study.

The improvement seen in the control may be attributed to the observed phenomenon that insertion of a needle into a painful area without drug delivery (dry needling), will result in some relief from pain symptoms. However, the significantly larger improvements in elbow function and pain level clearly demonstrate the efficacy of the APEX treatments that are an aspect of the present invention.

Figure 4:
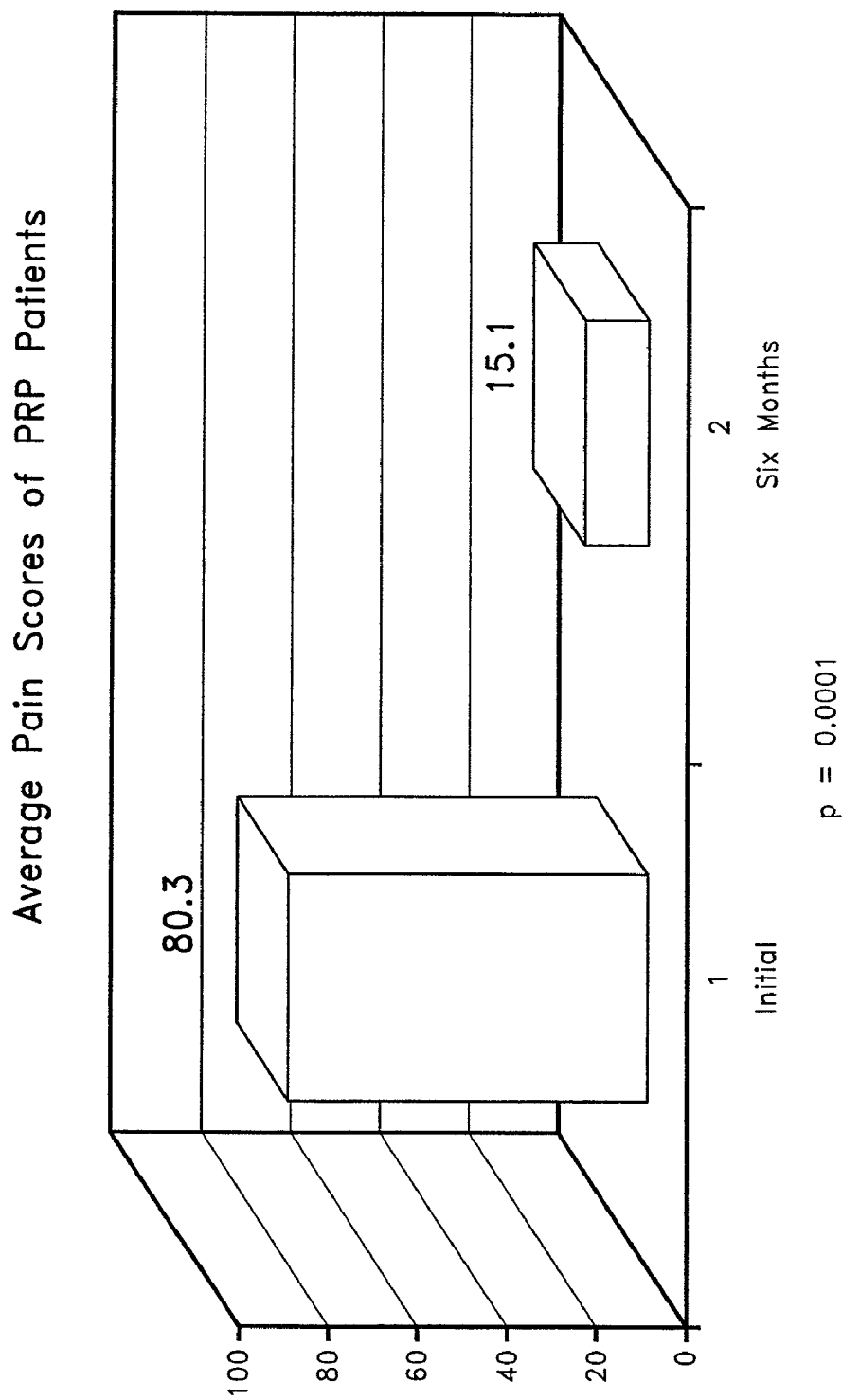
FIG. 4 shows average visual analog pain scores before treatment and at 6 months post-treatment (N=15) for tennis elbow.
Figure 5:
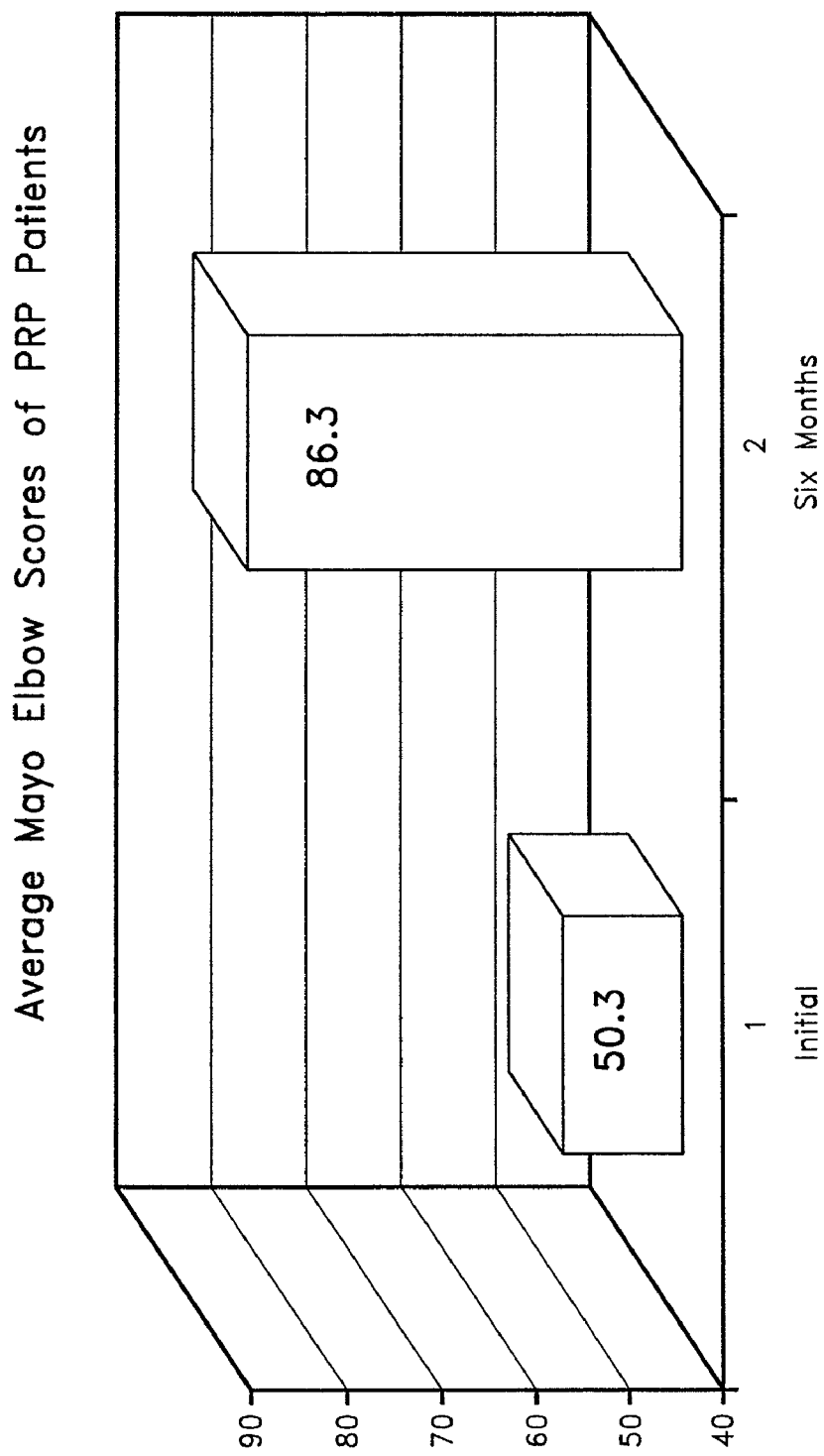
FIG. 5 shows the average Mayo elbow scores before treatment and at 6 months post-treatment (N=15) for tennis elbow.

The patients who had received the APEX treatment were again evaluated at six months. FIG. 4 shows the average pain scores of the PRP treated patients. At six months, there was an 81% improvement in visual analog pain scores. FIG. 5 shows a similar dramatic improvement in Mayo elbow scores which was a 72% improvement. At 6 months, 87% of the APEX patients were in the good or excellent category by the Mayo elbow score. All individuals were initially either fair or poor.

APEX has also been used to augment several tendon surgeries including Achilles tendon repairs, patellar tendon repair, quad tendon repair, and triceps tendon repair with similar positive results (data not shown).

Example 5

A patient presents with Plantar fasciitis. 30-60 cc of whole blood is withdrawn from a peripheral vein. APEX is prepared as described in Example 1. Basically, platelet-rich plasma is processed from the blood by centrifugation using the Cell Factor Technologies GPS machine (or any other commercial machine) to process the blood according to the manufacturer's protocol. PRP is buffered to physiologic pH using 8.4% sodium bicarbonate to provide APEX.

The area of maximal tenderness and pathology is identified by clinical examination or image guidance (Ultrasound, MRI, CT). The area is prepared with a skin antiseptic. A local field block is applied with marcaine.

APEX is injected using a small gauge needle into and around the area of pathology of the plantar fascia. The area is dressed sterilely. The patient is instructed to avoid weight bearing on the treated area for 2 days. A stretching protocol is initiated at 48 hours.

Example 6

A patient presenting with Achilles tendinosis is given 5 mg of Valium p.o. 30 minutes prior to the inventive tendon procedure. The patient is then prepped and draped in a sterile manner. A local anesthetic of 0.5% bupivicaine with epinephrine is infiltrated into the skin, subcutaneous structures and Achilles tendon. Care is taken to keep the local anesthetic out of the ankle joint.

Two to three minutes after administration of the local anesthetic, approximately 3-5 cc of the APEX composition of Example 1 is introduced into the Achilles tendon just above the ankle via a 22 gauge needle. Multiple punctures into the tendon approximately 0.5-1 cm from its insertion are made. Promptly after the minimally invasive introduction of the platelet composition of Example 1, the patient's lower leg and foot are immobilized without elevation of the leg. The surgical area is then sterilely dressed and the patient is asked not to move their leg for 30 minutes. The patient's neurovascular, pain and function status is evaluated shortly after the injection, and at 30 minutes following the end of the procedure. The patient is given oral narcotic pain medication as needed for the first 24-48 hours after the procedure. The Achilles tendon remains immobilized for one week following the procedure, followed by an formal postoperative stretching and strengthening program initiated at 8-10 days after the procedure.

Example 7

A patient presenting with a medial collateral ligament tear of the elbow is given 5 mg of Valium p.o. 30 minutes prior to the inventive tendon procedure. The patient is then prepped and draped in a sterile manner. A local anesthetic of 0.5% bupivicaine with epinephrine is infiltrated into the skin, subcutaneous structures and medial collateral ligament at the elbow. Care is taken to keep the local anesthetic out of the elbow joint.

Two to three minutes after administration of the local anesthetic, approximately 3-5 cc of the APEX composition of Example 1 is introduced into the medial collateral ligament at the elbow via a 22 gauge needle. Multiple punctures into the ligament approximately 0.5-1 cm from its origin are made. Promptly after the minimally invasive introduction of the platelet composition of Example 1, the patient's elbow and arm are immobilized at about 90% of flexion without elevation of the arm or hand. The surgical area is then sterilely dressed and the patient is asked not to move their arm for 30 minutes. The patient's neurovascular, pain and function status is evaluated shortly after the injection, and at 30 minutes following the end of the procedure. The patient is given oral narcotic pain medication as needed for the first 24-48 hours after the procedure. An optional formal post-operative stretching and strengthening program may be initiated at 2-3 days after the procedure.

Example 8

Cardiac Muscle

A patient presents with either an acute (i.e. heart attack) or chronic dysfunction (i.e. congestive heart failure) of cardiac muscle. An APEX composition is prepared as described in Example 1. Approximately 0.05 cc of an 8.4% sodium bicarbonate buffer per cc of extract is used to raise the pH to or slightly above 7.4. The extract is not activated through the addition of exogenous agent(s).

The APEX is then introduced into the area of dysfunctional cardiac muscle via a catheter. The APEX may also be combined with an implantable device such as a stent.

Example 9

Skeletal Muscle

A patient presents with weakness or atrophy of skeletal muscle. This could be the result of an injury or after a surgical procedure. Using the technique of Example 1, an autologous platelet extract (APEX) is obtained and buffered to physiologic pH.

The area of weakness or atrophy is identified and then after using 0.5% bupivicaine with epinephrine as a local anesthetic, the APEX is introduced into the muscle via a 22 g needle. This can be done a single time or it may require multiple injections. Postoperatively, the patient is started on a site specific stretching and strengthening protocol.

Example 10

Disc Material/Vertebral Bodies

A patient presents with low back pain and either bulging or black discs on an MRI scan. Using the technique of Example 1, an autologous platelet extract (APEX) is obtained and buffered to physiologic pH.

The disc in question is identified by X-ray guidance and then the APEX is introduced into the disc space via small gauge catheter. This procedure could be done alone or in combination with a thermal/radiofrequency ablation procedure. The APEX could also be injected into a vertebral body that has sustained a compression fracture with or without the use of a balloon prior to injection.

Example 11

Pancreas/Any Internal Organ

A patient presents with diabetes and poor insulin production. Using the technique of Example 1, an autologous platelet extract (APEX) is obtained and buffered to physiologic pH.

Under CT guidance and conscious sedation, the APEX is introduced via a small gauge catheter into the pancreas. The APEX is then injected into the islet cells to stimulate repair of these cells and thus restore insulin production.

Example 12

Brain/Spinal Cord

A patient presents with an acute neurologic deficit such as a spinal cord injury or stroke. Using the technique of Example 1, an autologous platelet extract (APEX) is obtained and buffered to physiologic pH.

Under MRI guidance and conscious sedation, the APEX is introduced into the area of injury or deficit. The APEX initiates or assists with repair of the locally damaged cells.

Example 13

Vascular Tissue

A patient presents with an area of hypovascularity in his or her lower extremities. The patient has a diagnosis of peripheral vascular occlusive disease. Using the technique of Example 1, an autologous platelet extract (APEX) is obtained and buffered to physiologic pH.

The area of hypovascularity is blocked with bupivicaine and then the APEX is introduced into either the muscle or soft tissue. The APEX induces angiogenesis, vascularization, and new blood vessel formation.

Example 14

Wound Healing

A patient presents with a chronic wound that is not healing properly. This could be a diabetic foot ulcer. Using the technique of Example 1, an autologous platelet extract (APEX) is obtained and buffered to physiologic pH.

The wound is carefully cleansed and debrided as needed. The APEX is then carefully injected into and around the chronic wound and its edges. It is held in place with an occlusive bandage or combined with an ointment. This process may be repeated as needed until the wound has healed.

Example 15

Neoplastic Tissue

A patient presents with either a benign or malignant tumor or process. Using the technique of Example 1, an autologous platelet extract (APEX) is obtained and buffered to physiologic pH. The APEX can be used either in vivo or in vitro to initiate or induce tumor cell death.

Specifically, the APEX is injected into a solid tumor with CT or MRI guidance via a small catheter. Alternatively, cancer cells after being grown in an APEX media could be reintroduced back into the body to attack and kill the remaining tumor. Without intending to be limited by theory, it is hypothesized that the APEX media has either the ability to cause tumor cell apoptosis (cell death) in vivo or it may have the ability to transform cancer cells into normal cells.

Example 16

Infections

A patient presents with a superficial or deep infection. Using the technique of Example 1, an autologous platelet extract (APEX) is obtained and buffered to physiologic pH.

The area of the infection is identified and the APEX is then directly applied or percutaneously introduced. This could be done under local or general anesthesia and with or without imaging guidance. The APEX typically has a concentrated number of white blood cells along with platelets. This combination of white blood cells and platelets either controls or eliminates an infection.

Example 17

Cell Cultures of Any Tissue

A researcher or clinician wishes to grow a cell culture of either fibroblasts or osteoarthritic cartilage cells. Using the technique of Example 1, an autologous platelet extract (APEX) is obtained and buffered to physiologic pH.

Figure 6:
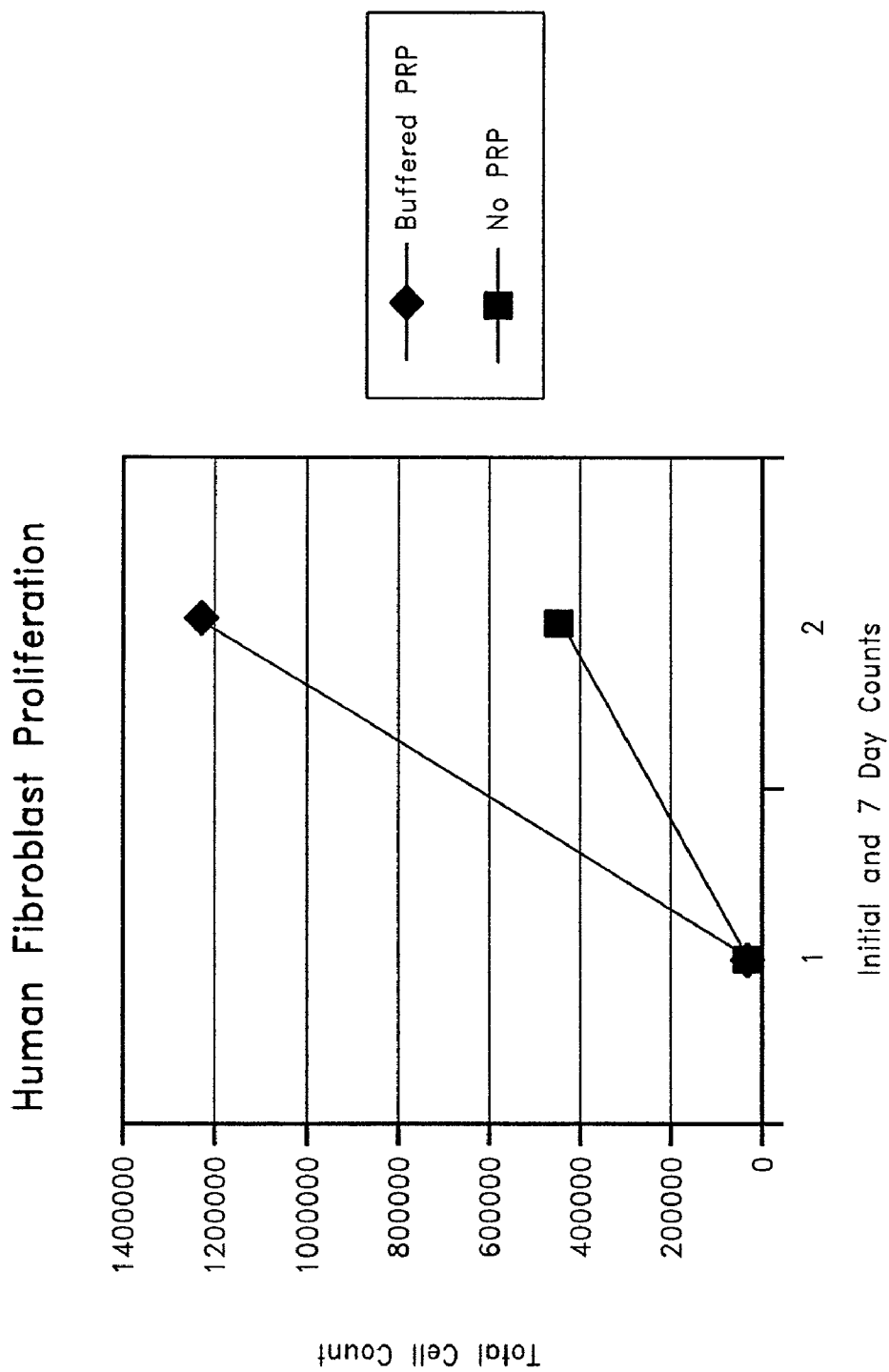
FIG. 6 shows initial and 7 day cell counts for human fibroblast cells in culture in the presence and absence of PRP.

Human fibroblast cells were cultured in 10% Fetal Bovine Serum ±Platelet Rich Plasma. As shown in FIG. 6, when APEX was present, the proliferation rate was 2.8 times higher at day 7. This result has been reproduced using different cell densities for fibroblast cells. Similar experiments using hematopoetic stem cells have shown a nine fold increase in cell number in the presence of APEX compared to control after eight days of culture (data not shown).

The cells are then isolated and grown in a media rich in the APEX in various conditions and dilutions. The APEX promotes cell differentiation and production of proteins such as collagen. The APEX may augment or promote the ability of the cells to transform into normal cells. Without intending to be limited by theory, it is hypothesized the APEX may convert the osteoarthritic cartilage cells to a more functional cell line that is reinjected into a diseased or injured joint. Alternatively, the APEX is directly introduced into an osteoarthritic joint to reverse the course of the disease. This is done under local anesthesia in a sterile manner.

Finally, the APEX may be used to help grow and differentiate any tissue or cell line in vivo or in vitro.

Example 18

Rotator Cuff Tendinosis

A patient presenting with a rotator cuff tendinosis is given 5 mg of Valium p.o. 30 minutes prior to the inventive tendon procedure. The patient is then prepped and draped in a sterile manner. A local anesthetic of 0.5% bupivicaine with epinephrine is infiltrated into the skin, subcutaneous structures and shoulder tendons.

Two to three minutes after administration of the local anesthetic, approximately 3-5 cc of the APEX composition of Example 1 is introduced into the shoulder tendons via a 22 gauge needle. Injection into more than one tendon may be required. Multiple punctures into the ligament approximately 0.5-1 cm from its origin are made. Promptly after the minimally invasive introduction of the platelet composition of Example 1, the patient's shoulder and arm are immobilized. The surgical area is then sterilely dressed and the patient is asked not to move their arm for 30 minutes. The patient's neurovascular, pain and function status is evaluated shortly after the injection, and at 30 minutes following the end of the procedure. The patient is given oral narcotic pain medication as needed for the first 24-48 hours after the procedure. An optional formal post-operative stretching and strengthening program may be initiated at 2-3 days after the procedure.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of vascularizing an area of tissue injury in a mammal comprising:
   drawing autologous blood from the mammal;
   adding an anticoagulant to the autologous blood;
   fractioning the autologous blood in a disposable separating tube using a centrifugation device to isolate a platelet-rich plasma composition;
   titrating the platelet-rich plasma composition to obtain a pH of about 6.5 to 8.0 creating a buffered platelet-rich plasma; and
   administering the buffered platelet-rich plasma to the area of tissue injury of the mammal, whereby platelet growth factors are released from the buffered platelet-rich plasma,
   wherein no exogenous activator is administered to the mammal or added to the platelet-rich plasma composition prior to its introduction to tissue with a compromised blood supply, and wherein the tissue with has a compromised blood supply comprises a tendinosis.

2. The method of claim 1, further comprising introducing a composition comprising a local anesthetic agent into the tissue before administering the buffered platelet-rich plasma composition.

3. The method of claim 1, wherein the mammal is selected from the group consisting of horses, cows, sheep, pigs, dogs and cats.

4. The method of claim 1, wherein the mammal is a human.

5. The method of claim 1, wherein the tendinosis is tennis elbow.

6. The method of claim 1, wherein the tendinosis is plantar fasciitis.

7. The method of claim 6, further comprising identifying an area to be treated using ultrasound.

8. The method of claim 7, wherein the buffered platelet-rich plasma composition is administered to a medial and/or central band of the identified fascia.

9. The method of claim 1, wherein the tendinosis is rotator cuff injury.

10. The method of claim 1, further comprising performing physical therapy to promote vascularization of the tendinosis.

11. A method of treating a tendinosis in a mammal consisting of:
    determining a site of tendinosis in the mammal;
    administering a composition consisting of an anesthetic selected from the group consisting of anbesol, benzocaine, lidocaine, procaine, and bupivicaine, to the tendinosis site; and
    administering a platelet-rich plasma composition without activator to the tendinosis site in the mammal.

12. The method of claim 11, further comprising titrating the platelet-rich plasma composition to obtain a pH of about 6.5 to 8.0.

* * * * *

UNITED STATES PATENT AND TRADEMARK OFFICE
CERTIFICATE OF CORRECTION

PATENT NO. : 7,608,258 B2 Page 1 of 1
APPLICATION NO. : 11/085987
DATED : October 27, 2009
INVENTOR(S) : Allan Mishra It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 430 days.

Signed and Sealed this

Twelfth Day of October, 2010

David J. Kappos
*Director of the United States Patent and Trademark Office*